United States Patent [19]

Fleischle

[11] Patent Number: Plant 5,830

[45] Date of Patent: Dec. 16, 1986

[54] DISTINCT VARIETY OF STREPTOCARPUS NAMED SELENA

[75] Inventor: Gerhard Fleischle, Vaihingen/E.-Ensingen, Fed. Rep. of Germany

[73] Assignee: Oglevee Associates, Inc., Connellsville, Pa.

[21] Appl. No.: 699,461

[22] Filed: Feb. 7, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus plant is characterized by its pure white color. It has smaller flowers and is more floriferous as compared to commonly grown Streptocarpus. It also has long permanence and is generally nonfertile.

1 Drawing Figure

BACKGROUND OF THE INVENTION

The present invention comprises a new and distinct cultivar of Streptocarpus X hybridus known by the varietal name of Selena. The new cultivar is a mutation brought about by the irradiation of a Streptocarpus known by the varietal name Hera (U.S. Plant Pat. No. 4,948 issued Nov. 16, 1982). The new cultivar is similar to Hera in respect of plant form and growth characteristics and is different from Hera in respect of color.

The new cultivar is generally characterized by its pure white color. It has smaller flowers and is more floriferous as compared to commonly grown Streptocarpus. It has long permanence and is generally nonfertile.

The new cultivar was discovered Oct. 28, 1981 in Vaihingen, Federal Republic of Germany; was first asexually reproduced by cuttings in Vaihingen, Federal Republic of Germany; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of eight weeks from a well-rooted young plant in a 2¼ inch pot to a flowering plant in a 6 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out by the Oglevee Floral Company in Connellsville, Pa. The plant history was taken on eight week plants blossomed under natural light in a greeenhouse and color readings were taken indoors under 100 foot candles of cool white fluorescent light. Color references are to the R.H.S. Colour Chart of The Royal Horticultural Society of London unless noted differently.

Botanical classification: Gesneriaceae (Family); Streptocarpus X hybridus (Genus X species).

Flower:

- *Fully expanded.*—5 to 6 centimeters.
- *Borne.*—In clusters of three to eight flowers per flower stalk above the foliage. Flower stalk arises from mid-rib of each leaf.
- *Stem.*—Single, long, pubescent and round.
- *Form.*—Funnel formed in an umbel.
- *Permanence.*—Long lasting 21 to 25 days.

Color:

- *Tonality from a distance.*—White with a lilac 44 veined throat (Exotica III).
- *Front of petals.*—White with veining, Fan 2 Purple Group 76A from the throat into the base of the petal and slightly outward therefrom.
- *Reverse of petals.*—White.
- *Throat.*—Two streaks of Fan 1 Yellow Group 3C.
- *Discoloration.*—Insignificant.

Petals:

- *Texture.*—Smooth.
- *Appearance.*—Individually lobed with smooth margins and reflexed end portions.
- *Arrangement.*—Regularly united into an elliptical form.
- *Persistence.*—21 to 25 days and remains on plant in dry form until picked.
- *Fragrance.*—None.

Reproductive organs:

- *Anthers.*—Two per flower and interconnected; imperfect.
- *Filament.*—Attached to petals for a distance of 2 centimeters up from base and then free standing for 0.5 centimeter.
- *Pollen.*—Generally nonfertile.
- *Pistil.*—2 to 2.5 centimeters long.
- *Style.*—White, 1 centimeter long and pubescent.
- *Stigma.*—White, flattened and oval.
- *Ovaries.*—Green, 1 to 1.5 centimeters long and 2 millimeters wide.

Plant:

- *Form.*—Leaves rosette from a crown at the soil line.
- *Growth.*—A spreading, free flowing habit with leaves being elliptical.
- *Height from soil line.*—18 to 20 centimeters.
- *Spread.*—40 to 50 centimeters.

Foliage.

*Size.*—10 to 28 centimeters in length; 5 to 10 centimeters wide at widest point.

*Quantity.*—12 to 15 leaves.

*Shape.*—Elliptical.

*Top side.*—Fan 3 Green Group 137B.

*Under side.*—Fan 3 Green Group 139D.

*Ribs and veins.*—Pinnate.

*Rib and vein color.*—Fan 3 Yellow Green Group 145C.

*Margin.*—Cuneate.

*Leaf tips.*—Obtuse.

*Leaf base.*—Acute.

I claim:

1. A new and distinct variety of Streptocarpus substantially as herein shown and described.

* * * * *

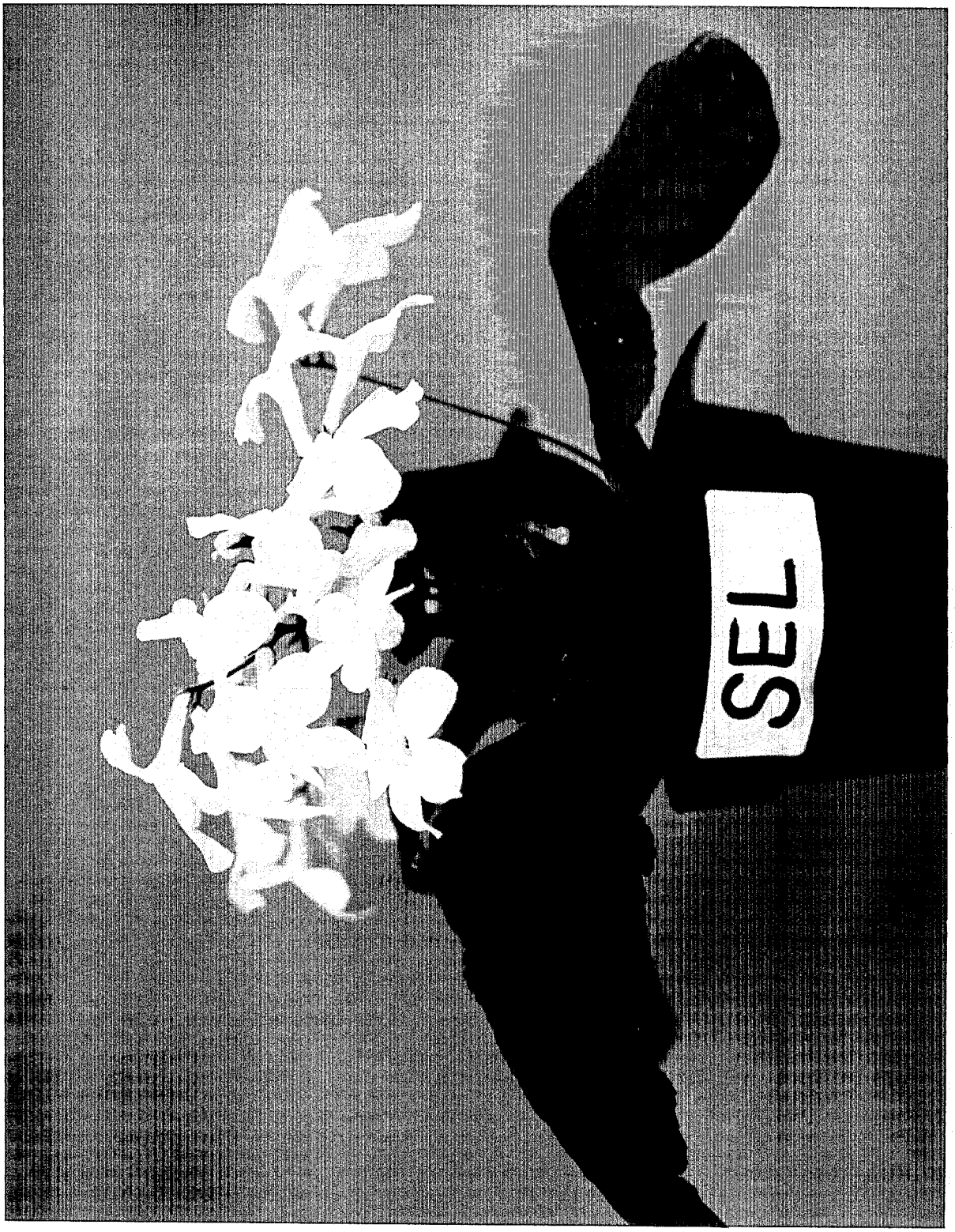
SEL